United States Patent [19]

Green et al.

[11] Patent Number: 5,725,538
[45] Date of Patent: *Mar. 10, 1998

[54] SURGICAL CLIP APPLIER

[75] Inventors: David T. Green, Westport; Henry Bolanos, East Norwalk, both of Conn.; Kenneth E. Toso, Portchester, N.Y.; Daniel E. Alesi, Sherman, Conn.; Robert Geiste, Milford, Conn.; Frank C. Maffei, Shelton, Conn.

[73] Assignee: United States Surgical Corporation, Norwalk, Conn.

[*] Notice: The term of this patent shall not extend beyond the expiration date of Pat. No. 5,720,756.

[21] Appl. No.: 713,772

[22] Filed: Sep. 13, 1996

Related U.S. Application Data

[63] Continuation of Ser. No. 492,863, Jun. 20, 1995, abandoned, which is a continuation of Ser. No. 134,017, Oct. 8, 1993, abandoned, which is a continuation-in-part of Ser. No. 959,201, Oct. 9, 1992, abandoned.

[51] Int. Cl.⁶ ........................................ A61B 17/00
[52] U.S. Cl. ........................ 606/143; 606/139; 227/901
[58] Field of Search ................................ 606/139, 142, 606/143, 151, 1, 205–208; 227/901, 19, 175.1–182; 29/243.56

[56] References Cited

U.S. PATENT DOCUMENTS

| | | |
|---|---|---|
| 2,968,041 | 1/1961 | Skold ........................... 606/143 |
| 3,152,336 | 10/1964 | Brady . |
| 3,232,089 | 2/1966 | Samuels et al. . |
| 3,646,801 | 3/1972 | Caroli . |
| 3,753,438 | 8/1973 | Wood et al. . |
| 3,777,538 | 12/1973 | Weatherly et al. . |
| 4,152,920 | 5/1979 | Green . |
| 4,201,314 | 5/1980 | Samuels et al. . |
| 4,202,480 | 5/1980 | Annett . |
| 4,242,902 | 1/1981 | Green . |
| 4,256,251 | 3/1981 | Moshofsky . |
| 4,296,751 | 10/1981 | Blake, III et al. . |
| 4,299,224 | 11/1981 | Noiles . |
| 4,316,468 | 2/1982 | Klieman et al. . |
| 4,317,535 | 3/1982 | Huftel et al. . |
| 4,325,376 | 4/1982 | Klieman et al. . |
| 4,372,316 | 2/1983 | Blake, III et al. . |
| 4,408,603 | 10/1983 | Blake, III et al. . |

(List continued on next page.)

FOREIGN PATENT DOCUMENTS

| | | |
|---|---|---|
| 0406724 | 1/1991 | European Pat. Off. . |
| 0469524 | 2/1992 | European Pat. Off. . |
| 0507537 | 10/1992 | European Pat. Off. . |
| 8801486 | 3/1988 | WIPO . |
| 9421181 | 9/1994 | WIPO . |

*Primary Examiner*—Jeffrey A. Schmidt

[57] ABSTRACT

A surgical clip applicator comprising a housing, a pair of handles pivotally connected to opposite sides of said housing, and a jaw blade assembly fixedly connected to the housing. The jaw blade assembly includes a pair of jaws for receiving and deforming a clip therebetween and a clip carrier for supplying a series of clips to said jaws. A channel assembly is slidably mounted in the housing and envelops said jaw blade assembly. A forming cam is connected between and to said handles and said channel assembly for sliding said channel assembly in a distal direction in response to closing of said handles together to move said jaws towards each other. A feed cam bar slidably mounted in said channel assembly in overlying relation to said clip carrier, said bar having a nose at its distal end. A pusher bar slidably mounted in said channel assembly for advancing clips along said clip carrier. A first spring member connected between said cam bar and said forming cam for sliding said cam bar in a proximal direction in response to closing of said handles together and further biasing said channel assembly in a proximal direction. Second spring member biasing said pusher bar in a distal direction to push a foremost clip in said clip carrier between said jaws in response to opening of said handles from each other. A clip retainer for preventing movement of said spring biased pusher bar is also provided.

48 Claims, 15 Drawing Sheets

U.S. PATENT DOCUMENTS

| | | |
|---|---|---|
| 4,424,902 | 1/1984 | Green . |
| 4,425,915 | 1/1984 | Ivanov .................................... 606/143 |
| 4,427,008 | 1/1984 | Transue . |
| 4,430,997 | 2/1984 | DiGiovanni et al. . |
| 4,452,357 | 6/1984 | Klieman et al. . |
| 4,452,376 | 6/1984 | Klieman et al. . |
| 4,462,404 | 7/1984 | Schwarz et al. . |
| 4,471,780 | 9/1984 | Menges et al. . |
| 4,478,220 | 10/1984 | DiGiovanni et al. . |
| 4,480,640 | 11/1984 | Becht . |
| 4,480,641 | 11/1984 | Fialla et al. . |
| 4,509,518 | 4/1985 | McGarry et al. .................. 606/143 |
| 4,512,345 | 4/1985 | Green et al. ....................... 606/143 |
| 4,522,207 | 6/1985 | Klieman et al. . |
| 4,532,925 | 8/1985 | Blake, III . |
| 4,549,544 | 10/1985 | Favaron . |
| 4,562,839 | 1/1986 | Blake, III et al. ................. 606/143 |
| 4,565,199 | 1/1986 | Becht . |
| 4,572,183 | 2/1986 | Juska . |
| 4,576,166 | 3/1986 | Montgomery et al. . |
| 4,586,503 | 5/1986 | Kirsch et al. . |
| 4,598,711 | 7/1986 | Deniga ................................ 606/143 |
| 4,611,595 | 9/1986 | Klieman et al. . |
| 4,616,650 | 10/1986 | Green et al. . |
| 4,624,254 | 11/1986 | McGarry et al. . |
| 4,630,608 | 12/1986 | Arroyo . |
| 4,637,395 | 1/1987 | Caspar et al. ....................... 606/143 |
| 4,662,373 | 5/1987 | Montgomery et al. . |
| 4,674,504 | 6/1987 | Klieman et al. . |
| 4,712,549 | 12/1987 | Peters et al. . |
| 4,733,664 | 3/1988 | Kirsch et al. . |
| 4,850,355 | 7/1989 | Brooks et al. . |
| 4,929,240 | 5/1990 | Kirsch et al. . |
| 4,983,176 | 1/1991 | Cushman et al. . |
| 5,030,226 | 7/1991 | Green et al. ....................... 606/158 |
| 5,047,038 | 9/1991 | Peters et al. . |
| 5,049,152 | 9/1991 | Simon et al. . |
| 5,084,057 | 1/1992 | Green et al. . |
| 5,104,395 | 4/1992 | Thornton et al. . |
| 5,112,343 | 5/1992 | Thornton . |
| 5,122,150 | 6/1992 | Puig . |
| 5,156,609 | 10/1992 | Nakao et al. ....................... 606/143 |
| 5,171,247 | 12/1992 | Hughett et al. ..................... 606/143 |
| 5,171,249 | 12/1992 | Stefanchik et al. . |
| 5,207,692 | 5/1993 | Kraus et al. . |
| 5,211,649 | 5/1993 | Kohler et al. . |
| 5,246,450 | 9/1993 | Thornton et al. . |
| 5,282,806 | 2/1994 | Haber et al. . |
| 5,330,487 | 7/1994 | Thornton et al. . |
| 5,370,658 | 12/1994 | Scheller et al. . |
| 5,409,498 | 4/1995 | Braddock et al. . |
| 5,431,668 | 7/1995 | Burbank, III et al. . |
| 5,501,698 | 3/1996 | Roth et al. . |

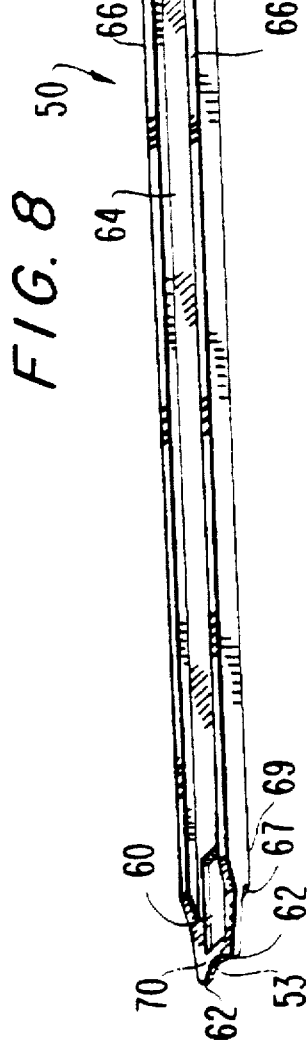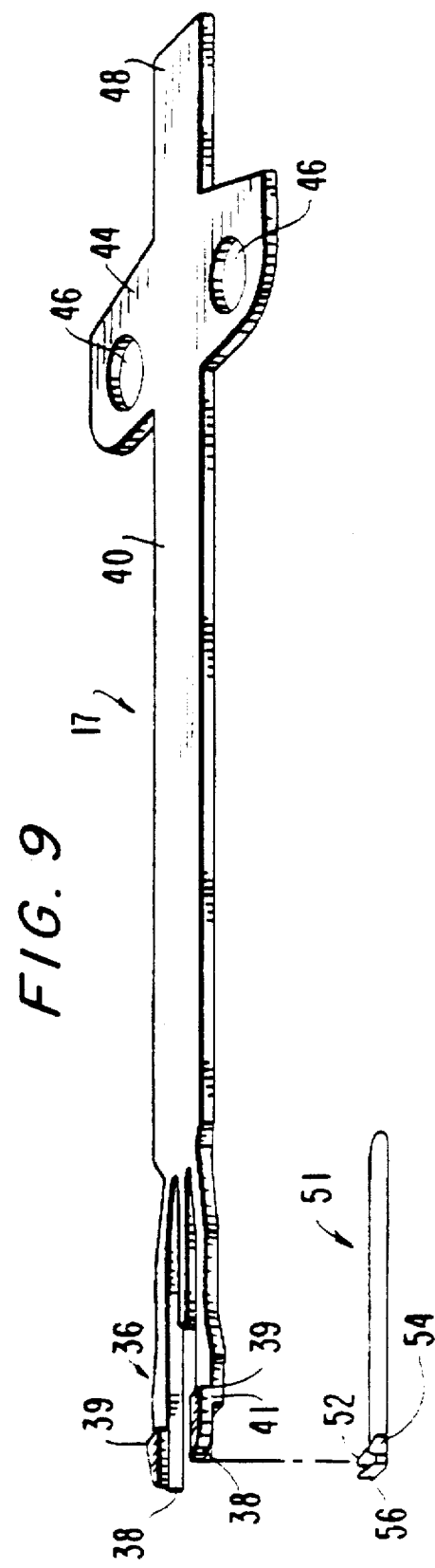

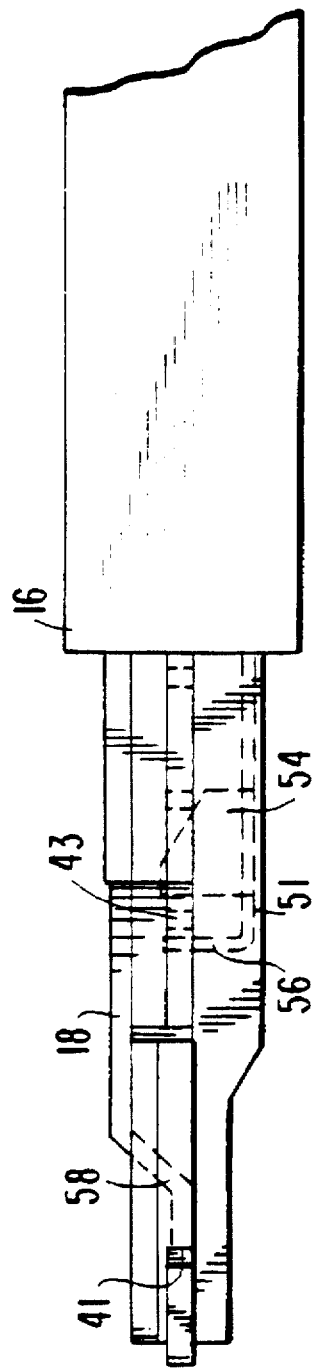
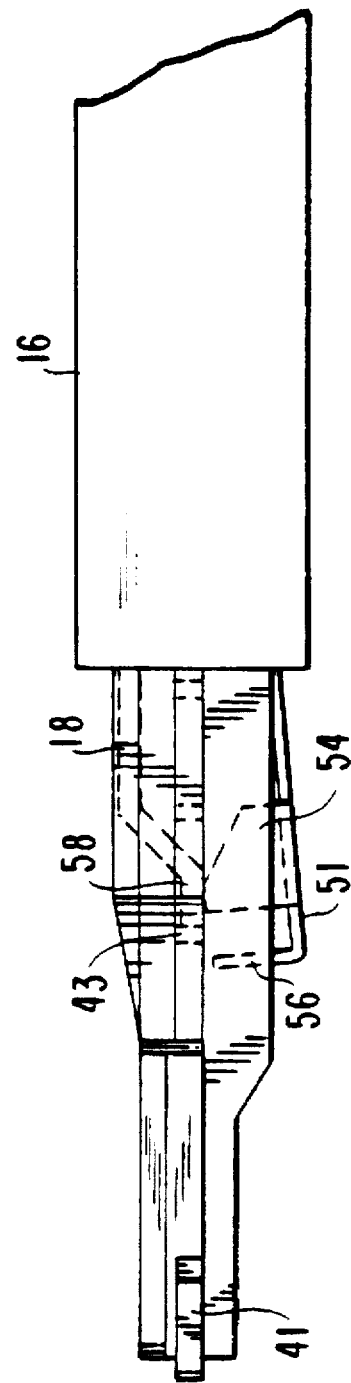

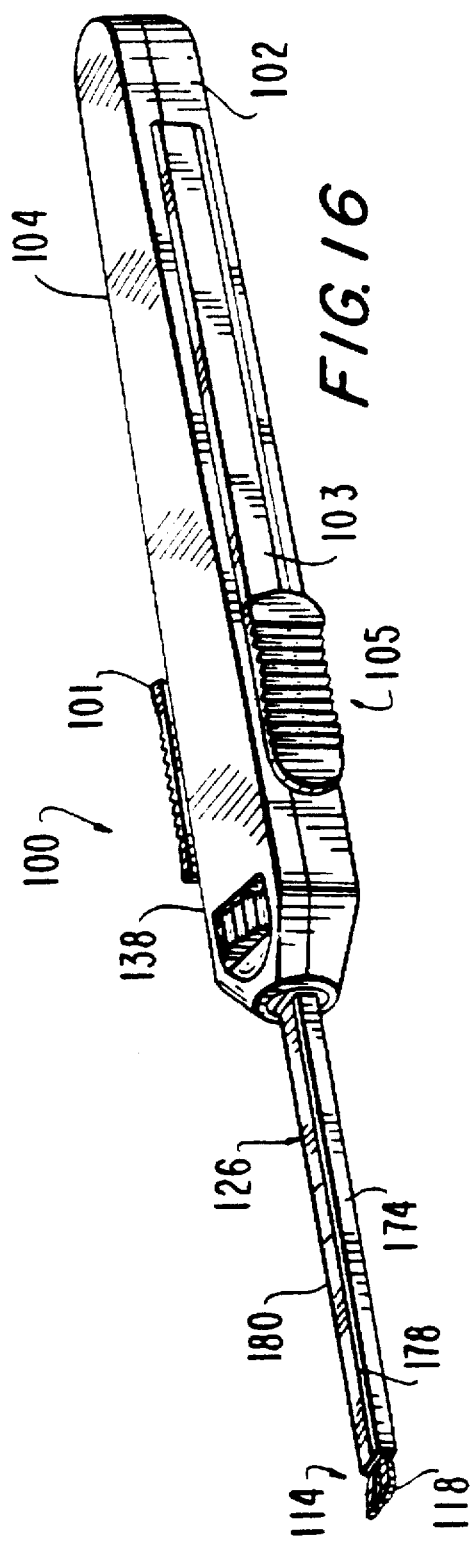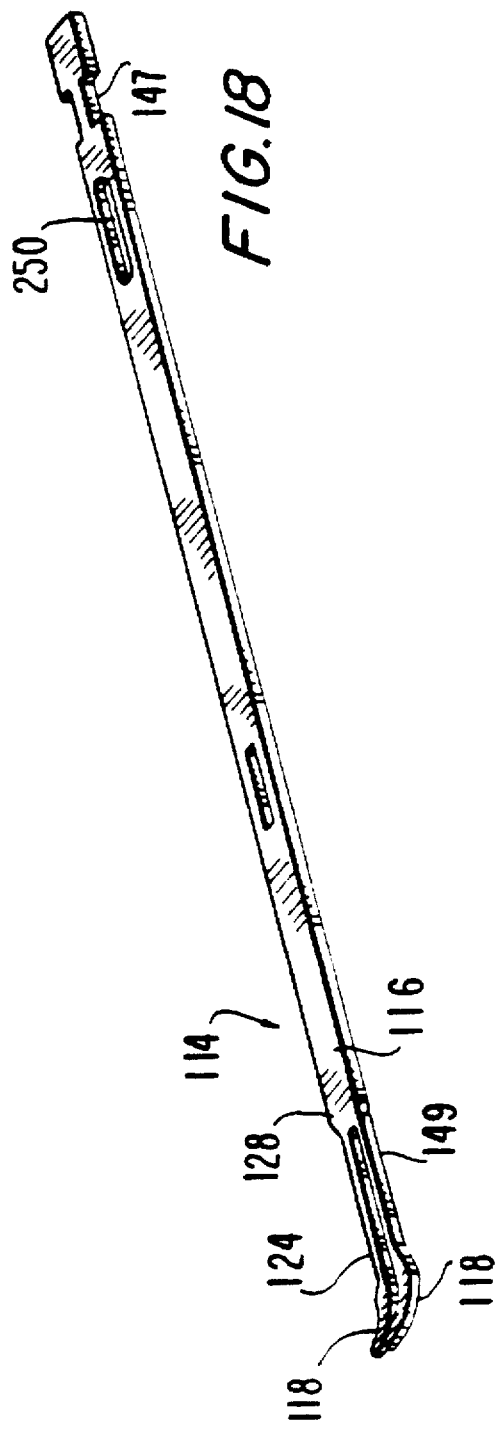

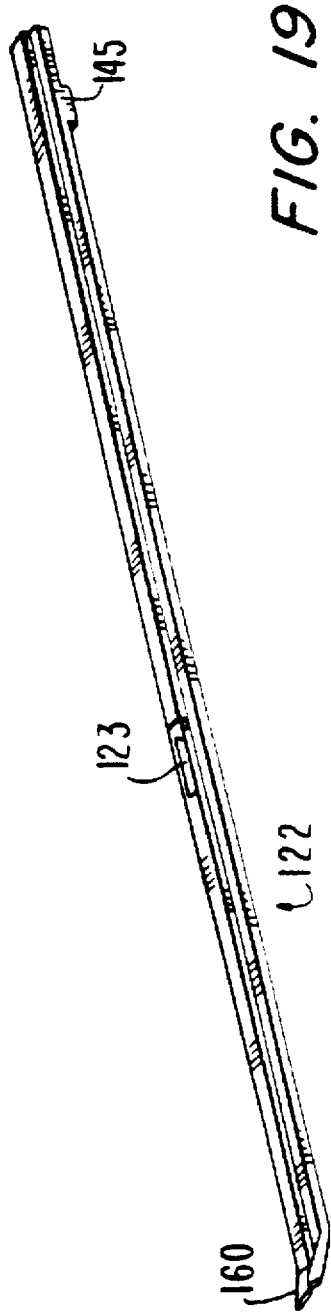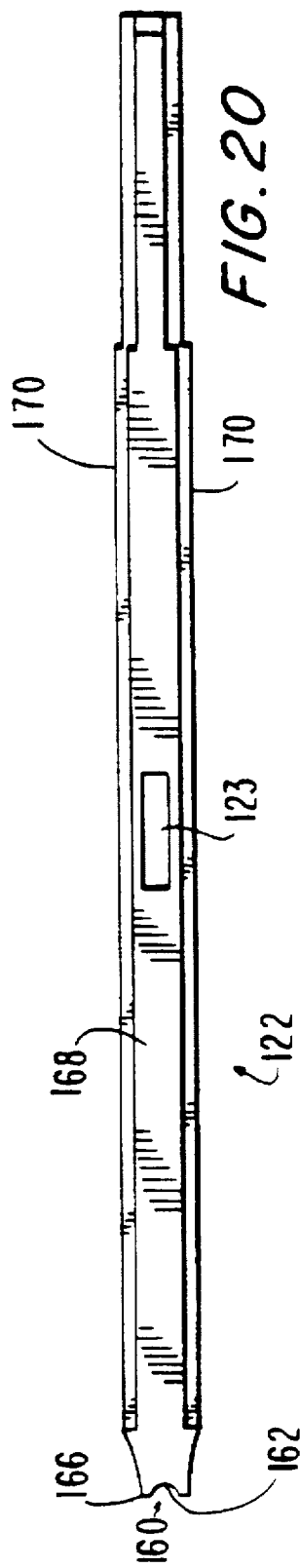

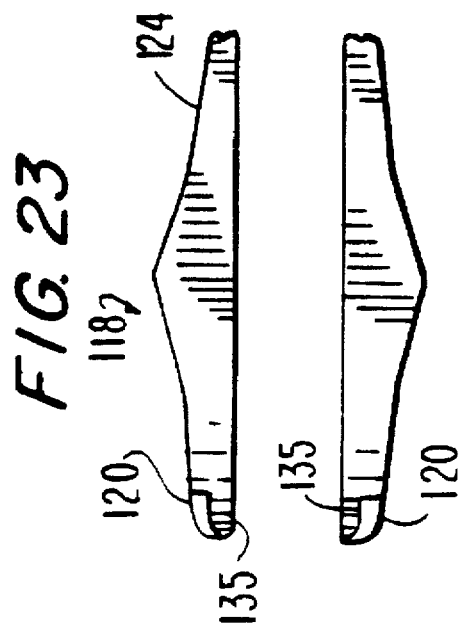
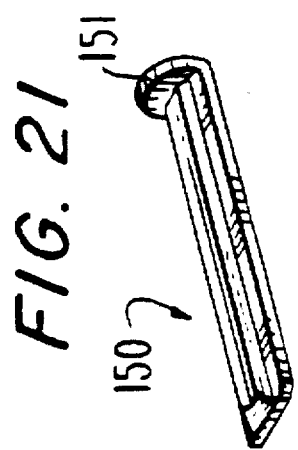
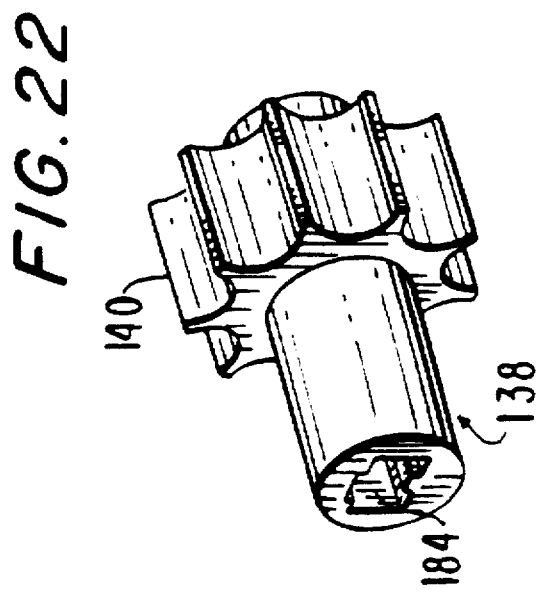

5,725,538

SURGICAL CLIP APPLIER

CROSS REFERENCE TO RELATED APPLICATIONS

This is a continuation of application Ser. No. 08/492,863 filed on Jun. 20, 1995 now abandoned, which is a continuation of application Ser. No. 08/134,017, filed on Oct. 8, 1993 now abandoned, which is a continuation-in-part of application Ser. No. 07/959,201 filed on Oct. 9, 1992 now abandoned.

BACKGROUND OF THE INVENTION

This invention relates to an instrument for applying a surgical clip in body tissue, and more particularly to an instrument for applying a surgical clip for anastomoses of a blood vessel.

The term "anastomosis" covers a variety of procedures in which blood vessels or other tubular members, such as parts of the colon, are joined or reconnected. Vessels may be joined in a variety of relative orientations, including end-to-end and end-to-side. Solid tubular structures such as peripheral nerves can also be joined together, as well as solid structures such as subcutaneous tissue and skin.

Anastomoses are performed by joining, clipping or suturing the vessels together at the juncture between them. When surgical clips are used, vascular anastomosis is achieved by approximating a pair of vessels, partially everting them and then joining the vessels by placing the arms of the surgical clip over the adjoined vessels. The arms of the surgical clip are then crimped about the tissue in such a way as to hold the vessel ends together without penetrating them.

Alternatives to conventional suturing process of joining vessels have been developed in order to prevent thrombosis which tends to occur at the points of penetration of the sutures. One such alternative, particularly for larger vessels, involves mechanical connectors such as collars. A second alternative to suturing is the use of surgical clips which are applied along the vessel juncture to perform a holding function similar to that of sutures, but without penetrating the vessel walls. Two such non-penetrating clips are shown in U.S. Pat. Nos. 4,586,503 and 4,733,664 to Kirsch et al. The former patent discloses a surgical microclip formed of plastically deformable metal or plastic material having minimal spring-back when crimped. The clip has a pair of parallel curved legs joined by a bridge at one end and terminating in rounded tips at the other end. The clip grips the edges of adjacent and everted tissue by crimping the legs together. The latter patent discloses a vascular surgical clip comprising a plastically deformable body portion, a tang for deforming the body, and a neck connecting the tang to the body, wherein the neck is designed to break upon application of a predetermined tensile force to the tang, and the body is designed to deform upon application to the tang of less than the predetermined tensile force.

As described in the above patents, the non-penetrating clips are applied over opposed edges of the vessels, the edges first being everted, or turned outward, to form flanges that are gripped between the jaws of the clips. Eversion not only enables the clip jaws to better grip the vessels, but also insures that only the interior surfaces of the vessels are in contact.

Vascular microsurgical clips are typically applied with a small hand-held tool that enables the surgeon to precisely place the clip over the tissue edges, and then to close the clip, as by applying a squeezing pressure to the tool. One example of a prior art clip applier for use in vascular microsurgery is disclosed in both U.S. Pat. Nos. 4,733,664 and 4,929,240 to Kirsch et al. These patents disclose a tool for applying a surgical clip, the tool including means for gripping and applying tension to the tang of the clip while also having means for simultaneously pushing against shoulders on the clip body. The tool disclosed in these patents requires that a clip be reloaded into the clip applier after each clip is fired.

The need exists for an improved surgical clip and particularly for an instrument for applying such a surgical clip which can be utilized for vascular anastomosis. One specific need is for an instrument that can hold a plurality of clips and automatically feed and apply the clips individually to the vessel. It would also be desirable for the instrument to be simple to manufacture, easy to manipulate and which applies the clips with consistent accuracy so as to provide a secure joining of vessels and tissue. Since the instrument is intended to apply clips during vascular anastomosis it would be desirable to configure it similarly to other vascular surgical devices, i.e. tweezers or pincer like implements, which are held between the thumb and forefinger of the user. One advantage of such a pincer like implement is that it enables the user to activate the instrument near the working distal end, thereby providing improved tactility and stability.

SUMMARY OF THE INVENTION

The present invention provides an instrument for applying a surgical clip to a blood vessel during a microsurgical anastomosis procedure. The clip applicator is designed for storage of multiple clips, and individual, automatic feed of the clips into the jaws of the instrument. Further, the applicator is designed to be similar in design to other instruments used during vascular surgical procedures, i.e. to be like a tweezer or other pincer like implement.

The invention provides a surgical clip applicator which is constructed with a pair of jaws for receiving and deforming a clip therebetween, a clip holding means having a series of clips for delivery to the jaws, a feed bar having a nose at a distal end and means for sequentially moving the feed bar from an initial distal-most position with the nose behind a clip positioned between the jaws to a proximal-most position behind a foremost clip of the clip series. A pusher bar moves the series of clips distally.

The means for sequentially moving the feed bar is a pair of handles which are connected to the feed bar and which are movable between an open position corresponding to the distal-most position of the nose and a closed position corresponding to the proximal-most position of the nose.

The handles are oppositely and pivotally connected at the proximal end of the housing and are actuated at their distal ends, thereby improving the tactility and visibility of the working end of applier, as well as the stability of the instrument. In addition, the jaws are part of a jaw blade assembly which is fixedly connected to the housing. A channel assembly is slidably mounted in the housing to envelope the jaw blade assembly with the feed bar slidably mounted in the channel assembly in overlying relation to the clip holding means. In operation, the applicator initially has a clip positioned between the jaws. Thus, a surgeon places the jaws of the applicator about a vessel and then squeezes the handles together. In response to closing of the handles the channel assembly is moved in a distal direction thereby closing the jaws to crimp the clip. At the same time, the feed bar is moved in a proximal direction to a position behind the foremost clip in the carrier. Once the handles are released, the feed bar moves in the distal direction to push the foremost clip to a position between the jaws. The applicator is then ready for application of the next clip.

A spring is provided in the housing for biasing the feed bar in a distal direction and for biasing the channel assembly in a proximal direction such that the handles are also biased into an opened position. A clip retainer is provided to prevent movement of the pusher bar which moves the stack of clips positioned on the clip holding means.

In another embodiment, the clip applicator includes a rotation knob for rotating the channel, jaw blade assembly, clip cover and clips independent of the handle. This clip applicator also includes a window for viewing a clip indicator which displays approximately how many clips remain in the device. Further, the tip of the jaws are angled approximately 30 degrees for better visibility during application of the clip.

BRIEF DESCRIPTION OF THE DRAWINGS

The present invention will be more fully appreciated as the same becomes better understood from the following detailed description of the present invention when considered in connection with the following drawings in which:

FIG. 8 shows an enlarged perspective view of the clip cover of the present invention;

FIG. 9 shows an enlarged perspective view of the jaw blade assembly and clip retainer of the present invention;

FIG. 12 shows a side view of the distal end of the instrument illustrating positioned but unformed clip in the jaws of the present invention;

FIG. 13 shows a side view of the distal end of the instrument illustrating the position of the clip retainer and feed bar after the clip has been formed in the jaws of the present invention;

FIG. 16 is a perspective view of the instrument according to another embodiment of the present invention;

FIG. 18 is an enlarged perspective view of the jaw blade assembly of FIG. 17;

FIG. 19 is an enlarged perspective view of the clip cover assembly of FIG. 17;

FIG. 20 is an enlarged detailed top view of the clip cover assembly of FIG. 17;

FIG. 21 is an enlarged perspective view of the wedge of FIG. 17;

FIG. 22 is an enlarged perspective view of the knob of FIG. 17;

FIG. 23 is an enlarged, partial top view of the distal end of the jaw blade assembly of FIG. 17;

DESCRIPTION OF THE PREFERRED EMBODIMENT

Figure 1:
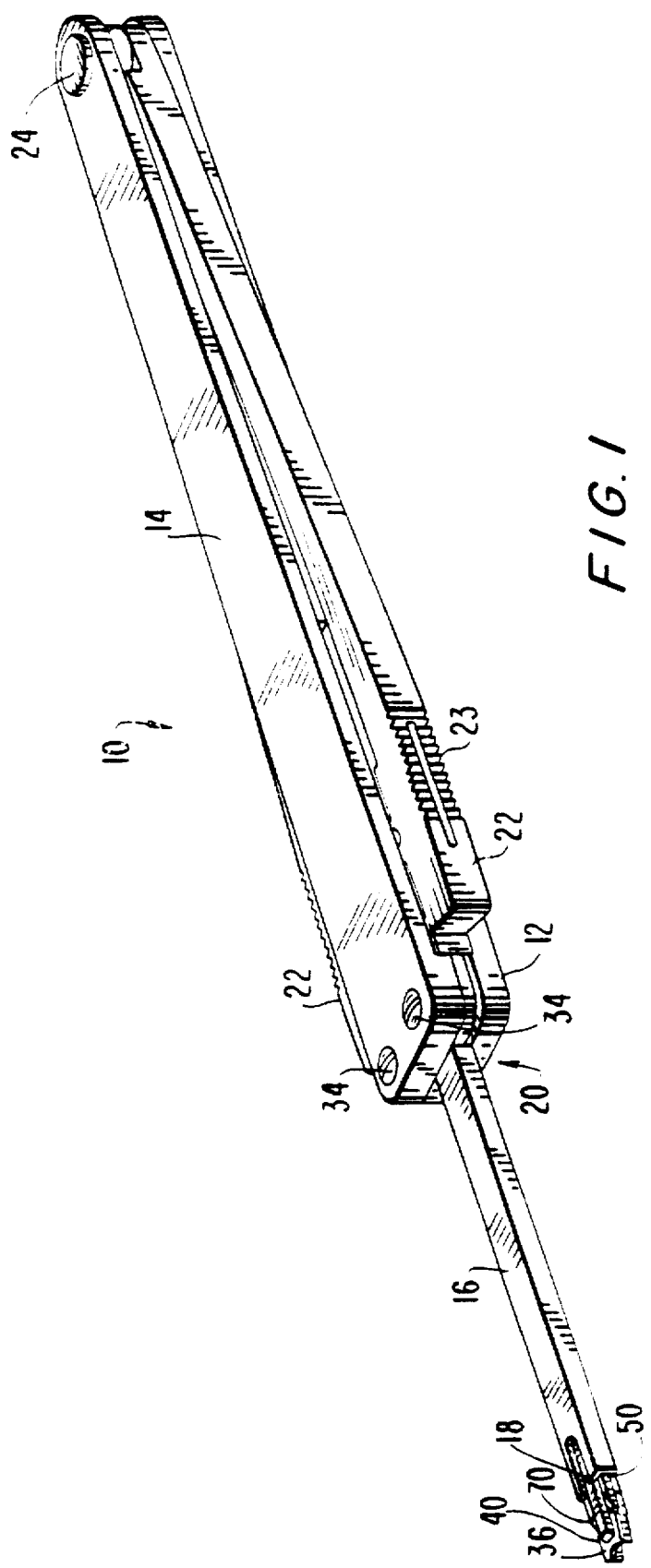
FIG. 1 illustrates a perspective view of the instrument of the present invention.
Figure 2:
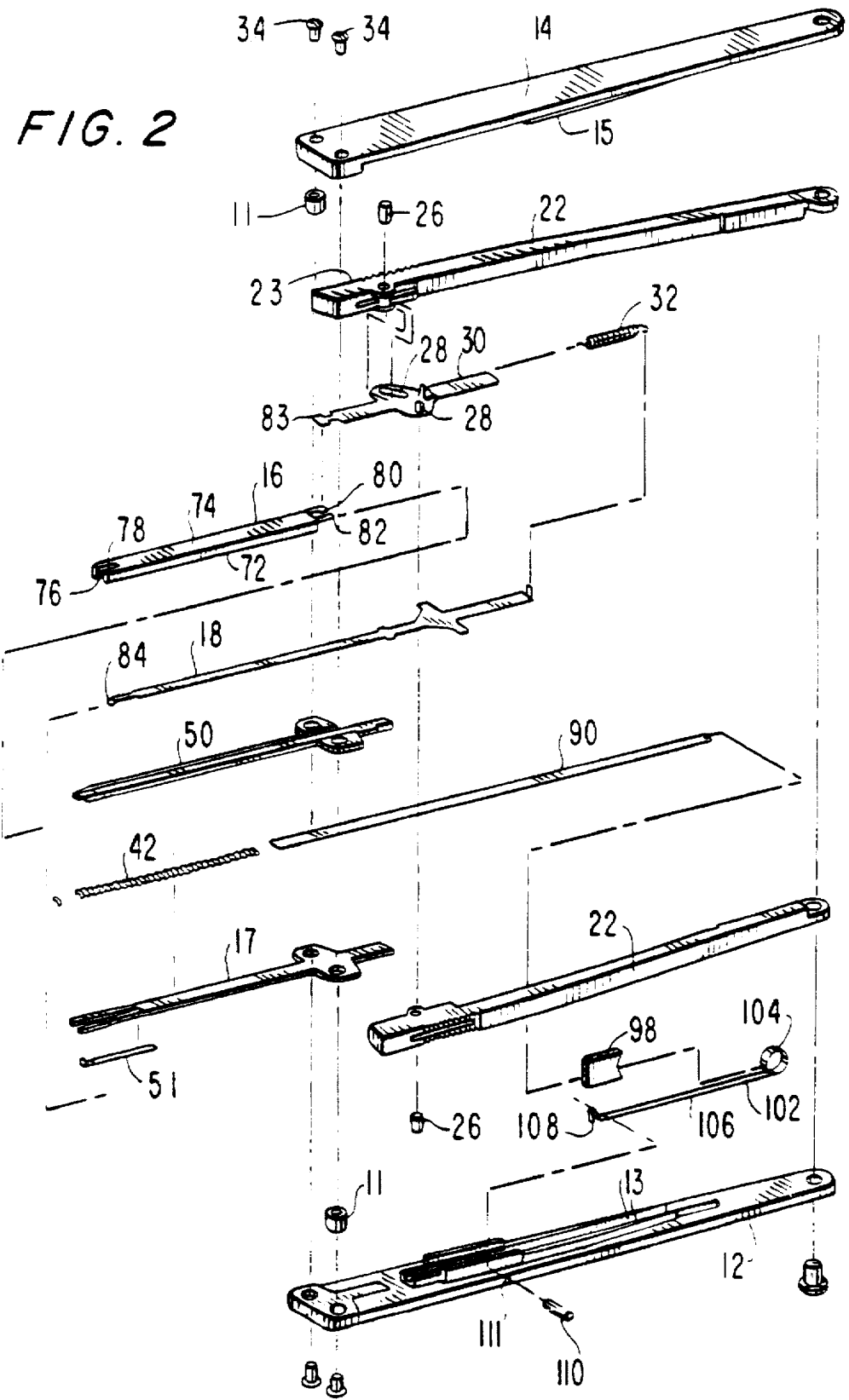
FIG. 2 illustrates an exploded perspective view of the instrument of the present invention.

Referring to FIGS. 1 and 2, the surgical clip applier 10 of the present invention includes a bottom housing 12, a top housing 14, a jaw blade assembly 17 having a pair of jaws, a channel assembly 16 slidably mounted in housings 12, 14, and a feed bar 18 slidably mounted in the channel assembly 16.

Referring to FIGS. 1 and 2, the bottom and top housings 12, 14 are secured together by pivot pin 24 and screws 34. The housings 12, 14 are of slender construction are made of any suitable material, for example, plastic material. As indicated, the inner surface 13 of the bottom housing 12 is contoured and recessed so as to receive various components of the applicator as further explained below. The inner surface 15 of top housing 14 is contoured for similar purposes. The pivot pin 24 extends through the proximal end of the housings 12, 14 and the proximal end of handles 22 to pivotally connect the handles 22 between the inner surfaces of the housings 12, 14 which are spaced apart to form a recess for receiving the handles 22. Spacers 11 are positioned in the housings 12, 14 to help form the recess between the housings 12, 14.

As shown in FIG. 1, the handles 22 are actuable at their distal ends 23; the end closest to the surgical site. This provides increased visibility, tactility and stability and enables the handles 22 to be held in a tweezer, or pincer like manner.

Turning now to the jaw blade assembly 17 for forming the clip and with reference to FIGS. 2 and 9, jaw blade assembly 17 includes an elongated jaw blade 36 which has a pair of jaws 38 formed at a bifurcated distal end for receiving a surgical clip therein. Each jaw 38 is provided with a small slot or groove in a side wall so as to receive therein a leg of the substantially C-shaped surgical clip 42 shown in FIGS. 14 and 15. Each jaw 38 also includes raised portions 39 which act as a stop for the clip cover 50 mounted thereon. The jaw blade 36 has a pair of camming surfaces 41 for engagement by channel assembly 16 to close the jaw in a manner described below.

Figure 14:
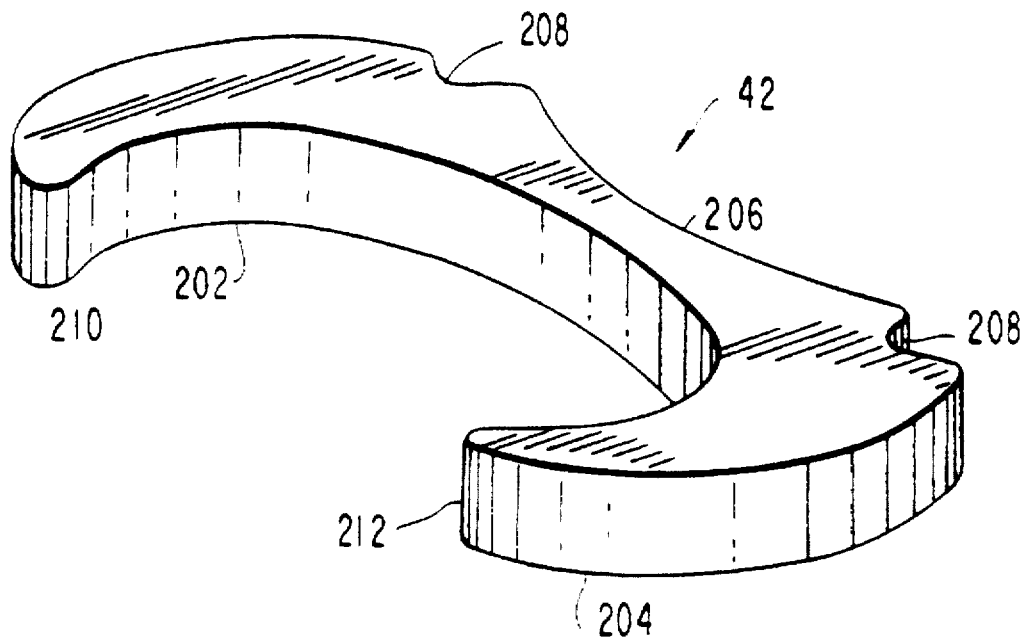
FIG. 14 shows an enlarged detailed perspective view of the clip of the present invention.
Figure 15:
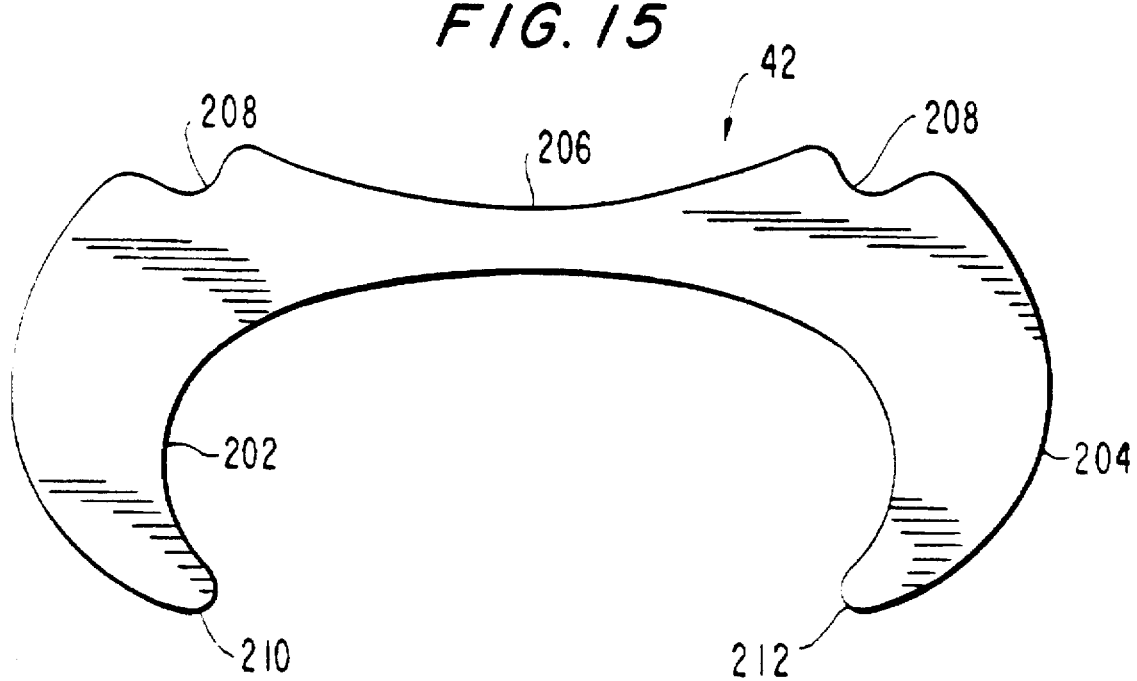
FIG. 15 shows an enlarged detailed top view of the clip of the present invention.

The jaw blade assembly 17 also includes along its elongated portion a clip carrier portion 40 for holding a series of clips 42 (shown in detail in FIGS. 14 and 15). In this embodiment the clip carrier portion 40 is integral with the jaw blade assembly 17, although multiple elements could be used to achieve the same result.

The proximal, or rear, end of the jaw blade assembly 17 includes a plate 44 having a pair of oppositely positioned openings 46 for receiving the screws 34 which retain the jaw blade assembly 17 within the housings 12, 14. A tail 48 is formed in the proximal-most end of the jaw blade assembly 17 for providing additional support for the pusher bar 90.

A clip retainer 51 is mounted under the distal end of jaw blade assembly 17. As shown in FIGS. 2 and 9, the distal end of the clip retainer 51 has a pair of oppositely positioned side walls 52 and 54 and a raised distal end wall 56. The clip retainer 51 prevents movement in the distal direction of the stack of clips 42 and is movable from a position preventing movement of stack of clips 42, as shown in FIG. 12, to a position in which the stack of clips 42 advance distally, as shown in FIG. 13.

Figure 11:
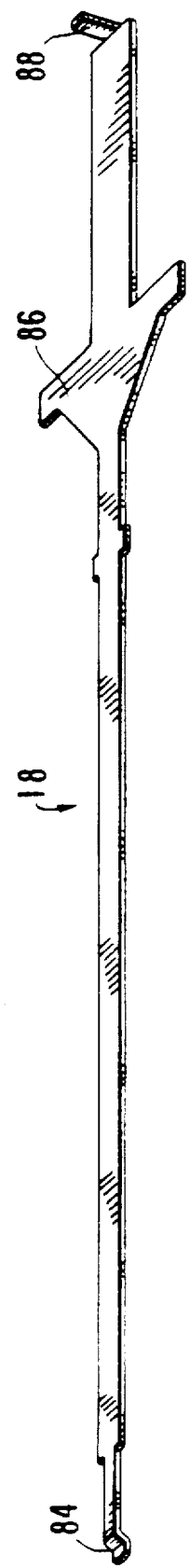
FIG. 11 shows an enlarged perspective view of the feed bar of the present invention.

As shown in FIGS. 2 and 11, the feed bar 18 is elongated and has a depending nose 84 at its distal end. Nose 84 moves clip retainer 51 into its activated position by engagement of the walls 52, 54 and 56 when the feed bar 18 has moved behind the second clip 43 in the stack of clips 42, but the first clip 41 is still in the jaws 38 of the jaw assembly.

As indicated, the distal end of the feed bar 18 is angled slightly downwardly with the tip bent up. Feed cam bar 18 functions to feed individual clips to the jaws and is positioned within the rails 64 (see FIG. 8) of the clip cover 50. Feed bar 18 further includes a pair of triangular projections 86 which cam the feed bar 18 and stabilize its connection to the housings 12, 14 and a proximal abutment 88 for receiving spring 32 as mentioned above.

Clip cover 50, shown in FIGS. 2 and 8, is elongated and similar, in shape to the jaw blade assembly 17 and functions as a tissue stop. The tissue stop 70 extends distally over the jaw blade 36. This tissue stop 70 has a bifurcated distal end which overlies and serves as a guide to prevent tissue from impeding movement of the clip 42 into the jaws 38. The cover 50 has a rounded cut out 53, a slot 60 and a pair of jaws 62 at its distal end. The pair of side walls or rails 66 provide a guide for the feed bar 18. The bottom surface 69 of the clip cover 50 is positioned atop jaw blade assembly 17 and includes a pair of downwardly extending side walls or rafts 67 between which the stack of clips 42 and the pusher bar 90 (see FIGS. 2 and 8) are provided.

Referring to FIGS. 1 and 2, the channel assembly 16, which as mentioned above functions to cam jaws 38 closed, includes an elongated channel shaped member 38 for enveloping the jaw blade assembly 17 and a pair of upstanding walls 72, a top wall 74 and a bottom wall 76. The top wall 74 and bottom wall 76 include a cutout 78 at their distal ends, and at the proximal end the top wall 74 includes recess 80 through which a projection 82 axially extends. The projection 82 engages an engagement member 83 of the forming cam 30 and thereby causes movement of the channel assembly 16 upon movement of the forming cam 30.

Figure 4:
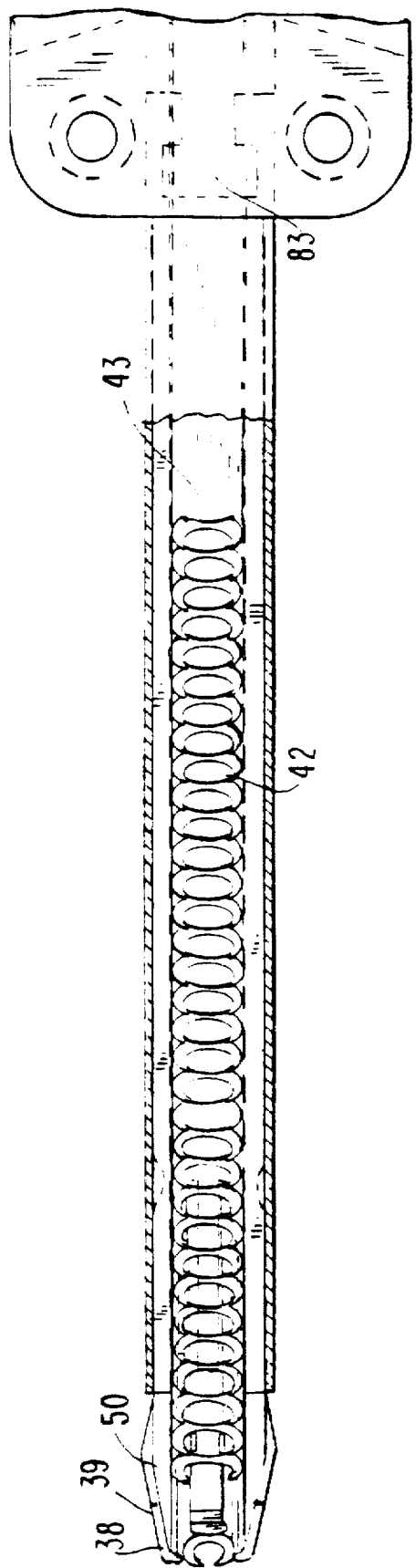
FIG. 4 shows a top view of the distal portion of the instrument of the present invention.
Figure 5:
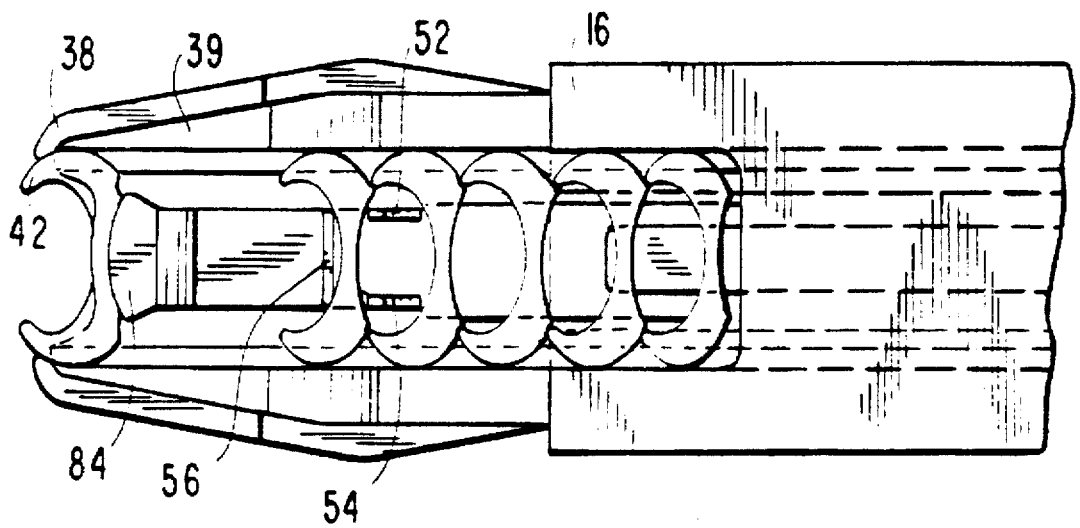
FIG. 5 shows a detailed top view of a unformed clip loaded in the jaws of the present invention.
Figure 6:
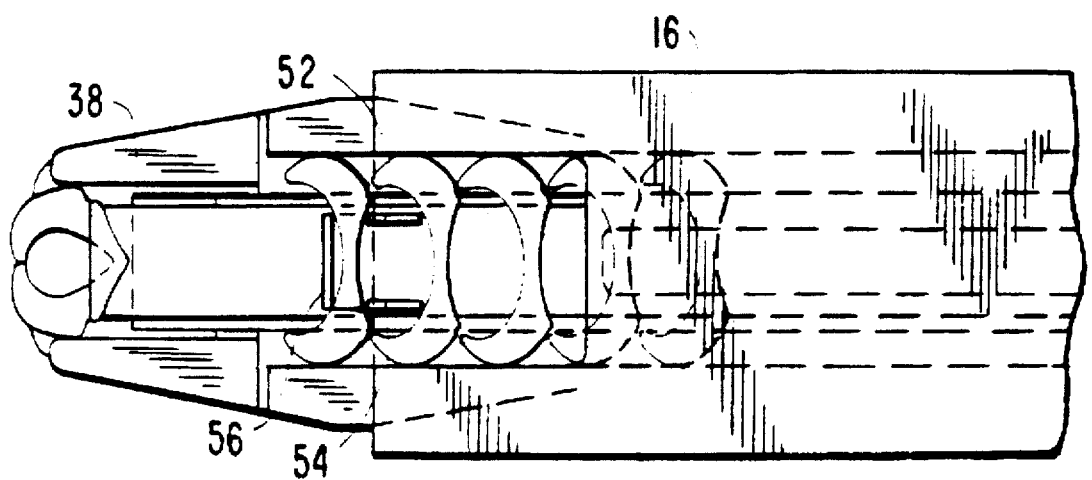
FIG. 6 shows a detailed top view of a clip loaded in the jaws of the present invention.
Figure 7:
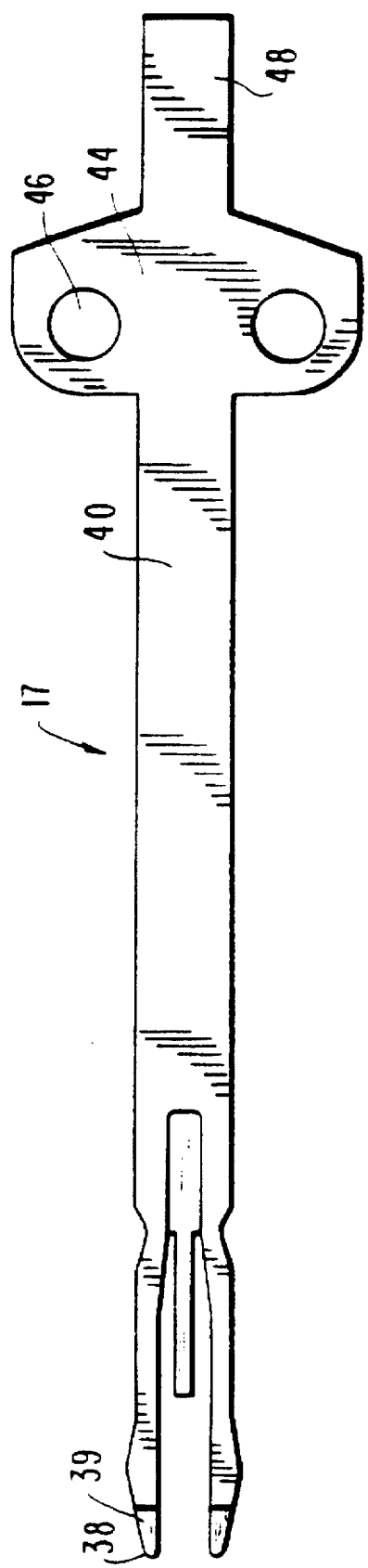
FIG. 7 shows an enlarged top view of the jaw blade assembly of the present invention.
Figure 10:
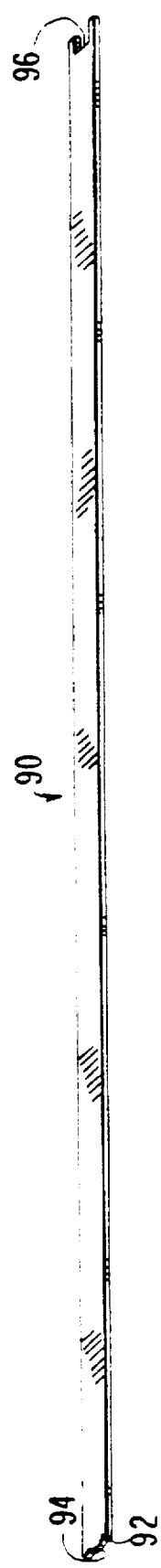
FIG. 10 shows an enlarged perspective view of the pusher bar of the present invention.

With reference to FIGS. 2 and 10, elongated pusher bar 90 has oppositely positioned projections 92 and a rounded member 94 extending from its distal end for engaging and pushing the last and most proximal clip 43 (see FIG. 4) on the clip carrier 40. The projections 92 engage the grooves 208 and the rounded member 94 engages the backspan 206 of the last clip 43. The proximal end of the pusher bar 90 includes a slot 96 for receiving a spring guide 98. A coil spring 302 fits within the molded contours of bottom housing 12. The channel 308 of spring 302 is engaged by the pin 310 which extends through an aperture 311 in the bottom housing 12. The feed spring 302 rolls along the top of the elongated portion 306 as the pusher bar advances the clips 42.

As shown in FIGS. 14 and 15, a surgical clip embodying the invention and designed for application by the clip applier 10 is formed of a unitary piece of biologically acceptable, plastically deformable material such as a noble metal (i.e. gold, silver, platinum, titanium etc.). While metal clips are presently preferred, it is contemplated that the other materials such as suitable polymer plastics may be used. The material, preferably titanium, is sufficiently ductile or plastically deformable so that when the clips crimped there is minimal spring-back. The clip is designed to apply contact force to the tissue regardless of tissue thickness.

The clip 42 includes a pair of inwardly curved arms 202' and 204' interconnected by a bridging section 206', the two arms extending generally parallel in one direction from the bridging section. The arms terminate at tips 210' and 212' which are rounded to prevent injury to the subject tissue. As described above, the bridge portion 206' includes a pair of grooves 208' for engaging the clip applier described above and for feeding the clips down the clip carrier in the applier.

The size of the clip will naturally vary according to the application, this invention is not limited to a particular size clip.

Figure 3:
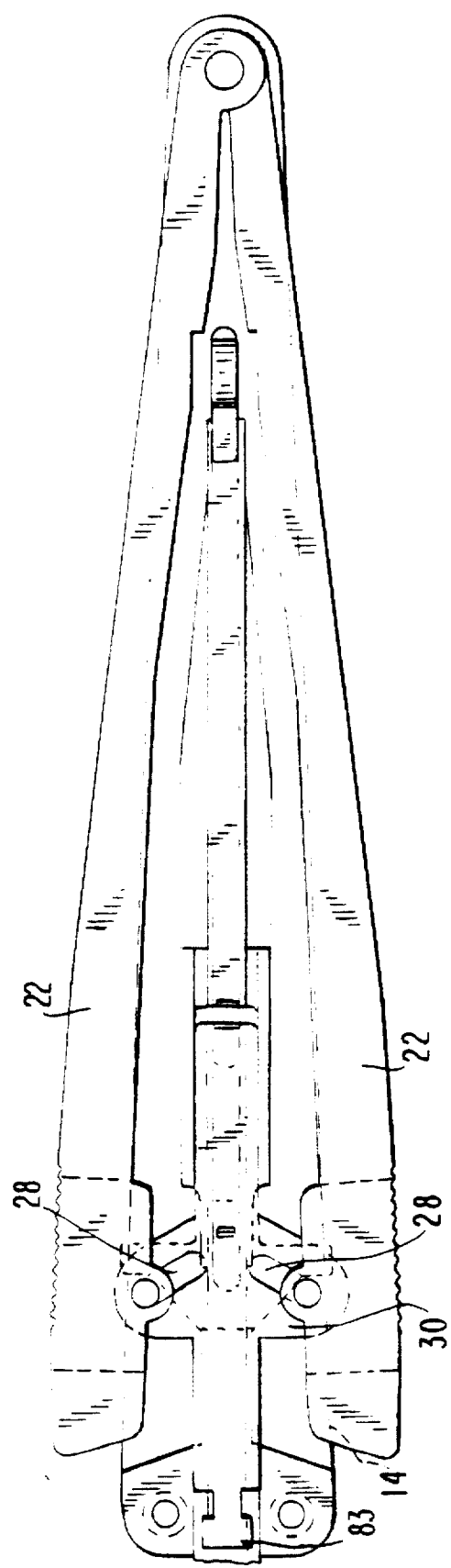
FIG. 3 illustrates a top view of the handle of the present invention.

Turning now to the actuating mechanism of the instrument and referring to FIGS. 1, 2 and 3, each handle 22 is articulated to the housings 12 and 14, the channel assembly 16, the feed bar 18 and the pusher bar 90 in a similar fashion. More specifically, handles 22 are pivotally connected to opposite sides of the housings 12, 14, by pivot pin 24 and by pins 26 which ride along cam slots 28 of forming cam 30. The forming cam 30 is connected at its distal end to the channel assembly 16, as is discussed in detail below, and at its proximal end to a spring 32. The other end of the spring is attached to the proximal end of the feed bar 18 and biases it in a distal direction. Thus, the spring 32 biases the channel assembly 16 and the forming cam 30 in a proximal direction, such that the handles 22 are biased in an open position. Since each handle is connected in a similar fashion, only the connection of one of the handles will be discussed. As indicated in FIG. 2, the channel assembly 16 is mounted at the distal end of forming cam 30 while the feed bar 18 is attached through spring 32 to the proximal end of forming cam 30. Thus, when handles 22 close together, the pins 26 move along slots 28 of forming cam 30 to distally advance the forming cam 30 which correspondingly advances the channel assembly 16 and overcomes the bias of spring 32. After the channel assembly 16 advances a slight distance distally, e.g. approximately 0.020 inch, the nose 84 of the feed bar 18 moves proximally to a position behind the next clip 42 in the clip carrier 40.

In use, the clip applier 10 is provided with a clip 42 already in the jaws 38 of the jaw blade assembly 17. To apply the clip, the handles 22 are first squeezed together overcoming the bias of spring 32 and causing the channel assembly 16 to move forwardly and the feed bar 18 to move rearwardly into a position to feed the second clip 43 from the clip carrier 40 as described above. As the channel assembly 16 moves forwardly and over jaws 38 of the jaw blade assembly 17, the jaws 38 are cammed closed to form the clip 41 therein. After the nose 84 of the feed bar 18 has moved behind the second clip 43, and the first clip 41 is fully formed in the jaws 36, the clip retainer 51 is biased downwardly by engagement with the nose 84 of feed bar 18. As the handles open and the clip retainer 51 continues to be biased downwardly, the feed cam 18 moves forward and advances the next clip 43 to the jaws 36. The downward biasing of the clip retainer 51 also permits the stack of clips 42, which are normally biased in a forward direction by spring 102, to advance forward and move distally.

Figure 17:
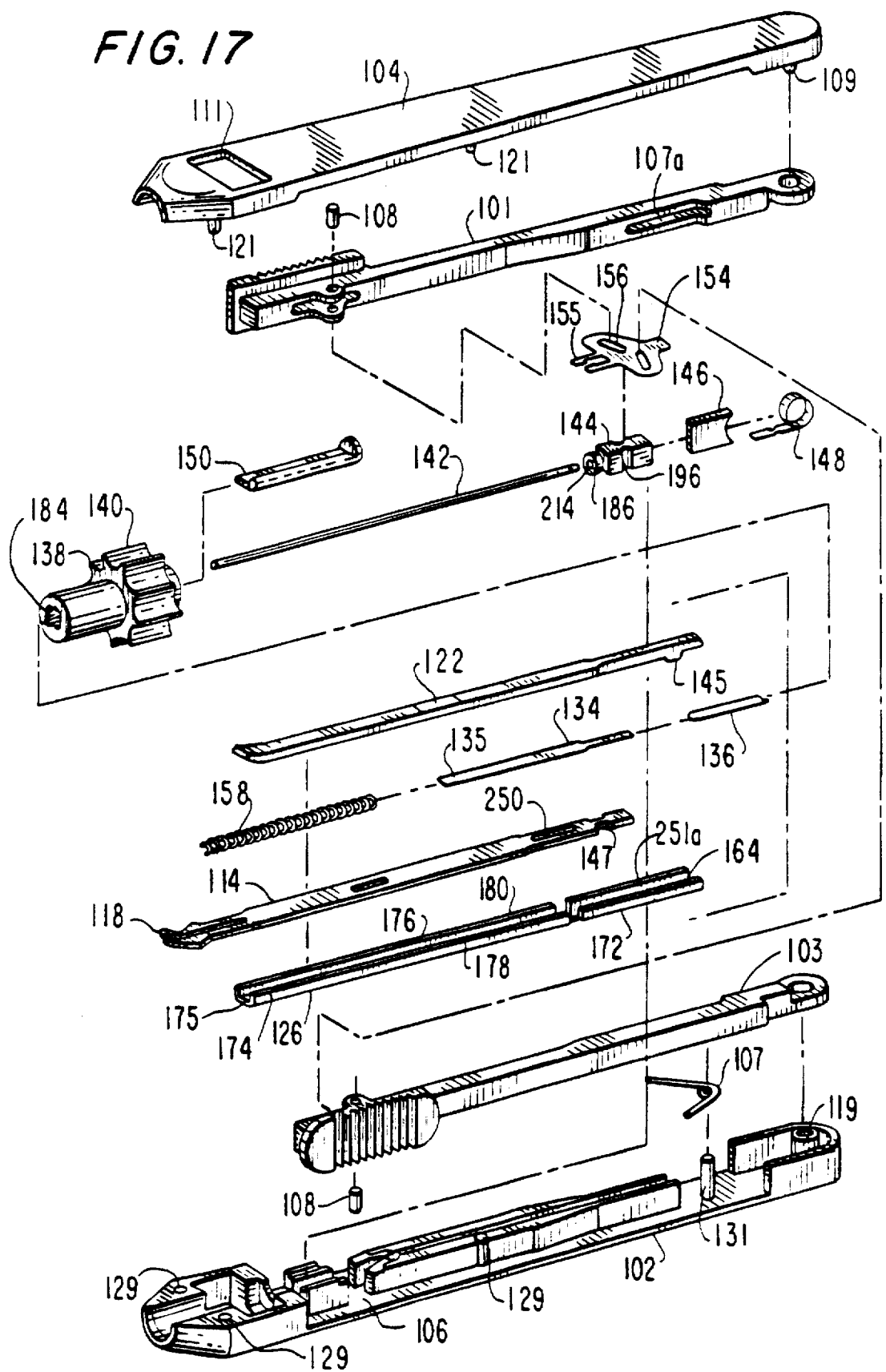
FIG. 17 is an exploded perspective view of the instrument of FIG. 16.

Referring to FIGS. 17 and 18, the surgical clip applier 100 of an alternative embodiment of the present invention includes a bottom housing 102, a top housing 104, a jaw blade assembly 114 having a pair of jaws 118, and a channel assembly 126 slidably mounted in housings 102, 104.

Referring to FIGS. 16 and 17, the bottom and top housings 102, 104 are press fit and held together by the engagement of pin 109 with the pin receiver 119 and by the engagement of pins 121 with slots 129, but alternatively may be welded. The housings 102, 104 are of slender construction are made of any suitable material, for example, plastic material. As indicated, the inner surface 106 of the bottom housing 102 is contoured and recessed so as to receive various components of the applicator as further explained below. The inner surface 106 of top housing 104 is contoured for similar purposes. The pivot pin 109 extends from the proximal end of the housing 104 to pivotally connect the handles 101, 103 between the inner surfaces of the housings 102, 104 which are spaced apart to form a recess for receiving the handles 101, 103. The housings 102, 104 also include a window 111 which receive the knob 138.

As shown in FIG. 16, the handles 101, 103 are actuable at their distal ends 105; the end closest to the surgical site. This provides increased visibility, tactility and stability and enables the handles 101, 103 to be held in a tweezer or pincer-like manner. The handles 101, 103 are biased outwardly by a spring 107 which is retained by the spring post 131 formed on the inner surface 106 of the bottom housing 102.

Figure 24:
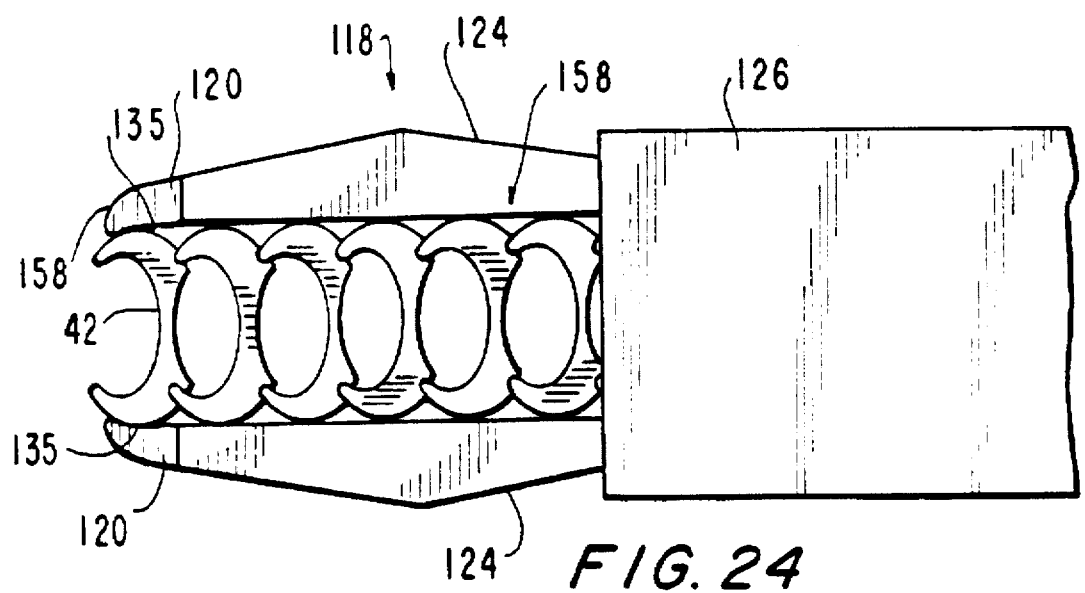
FIG. 24 shows a detailed top view of a unformed clip loaded in the jaws of the instrument of FIG. 17; and, FIG. 25 shows a detailed top view of a clip loaded and formed in the jaws of the instrument of FIG. 17.
Figure 25:
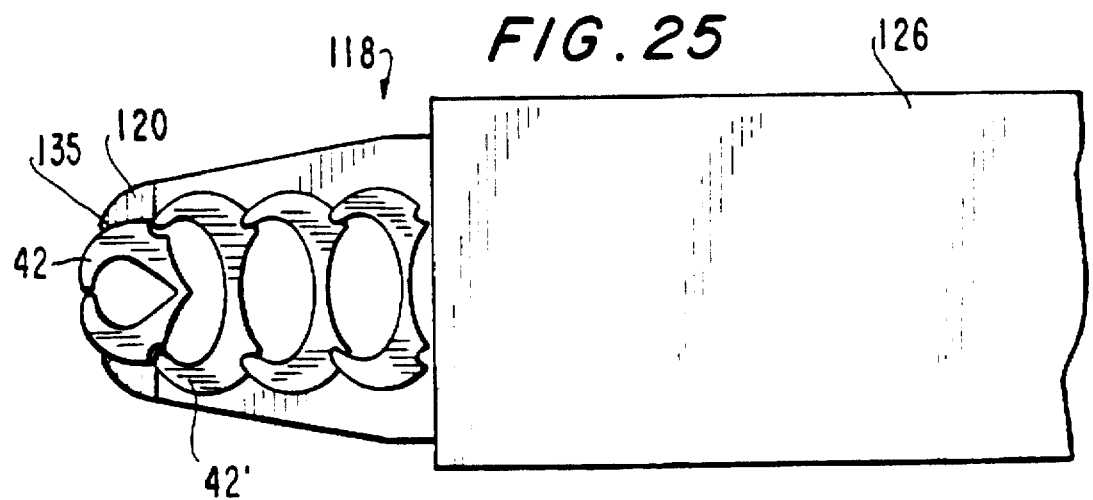

Turning now to the jaw blade assembly 114 for forming the clip 158 and with reference to FIGS. 17, 18, and 23 jaw blade assembly 114 includes an elongated jaw blade 116 which has a pair of jaws 118 formed at a bifurcated distal end for receiving a surgical clip therein. Each jaw 118 receives a leg of the substantially C-shaped surgical clip 158 as shown in FIGS. 24 and 25. Each jaw 118 also includes raised portions 120 which act as a stop for the clip 158 and enhance formation thereof. The raised portions 120 include an arcuate portion 135 which conforms in shape to the leg of the clip 158. The jaw blade 116 has a pair of camming surfaces 124 for engagement by channel assembly 126 to close the jaw 118 in a manner described below. The jaws 118 are bent at an angle of approximately 30 degrees to enhance visibility of the structure to which the clip 158 is being applied. Another feature of the jaws 118 is that they are flexible and deformable and preferably formed of stainless steel.

The jaw blade assembly 114 also includes along its elongated portion a clip carrier portion 128 for holding a series of clips 158 (shown in detail in FIGS. 24 and 25) which are retained in the side walls 170 of the clip cover 122. In this embodiment the clip carrier portion 128 is integral with the jaw blade assembly 114, although multiple elements could be used to achieve the same result.

Clip cover 122, shown in FIGS. 17, 19 and 20 is elongated and similar in shape to the jaw blade assembly 114 and functions as a tissue stop 160. The tissue stop 160 extends distally over the jaws 118. This tissue stop 160 has a bifurcated distal end which overlies and serves as a guide to prevent tissue from moving the clip 158 proximally and out of raised portion 120. The cover 122 has a rounded cut out 162, and a pair of jaws 166 at its distal end. The bottom surface 168 of the clip cover 122 is positioned atop jaw blade assembly 114 and includes a pair of downwardly extending side walls or rails 170 between which the stack of clips 158 are retained and the pusher bar 134 and indicator 136 are provided. The distal end of the clip cover 122 includes a pair of downwardly extending key portions 145 which engage cut outs 147 in the jaw blade assembly 147.

Referring to FIGS. 16 and 17, the channel assembly 126, which as mentioned above functions to cam jaws 118 closed, is U-shaped and includes a reduced height portion 172 for engagement with the rotation knob 138 and a slot 164 for engaging a link 144. The channel 126 envelopes the jaw blade assembly 114 and includes a pair of upstanding walls 174, 176 and a bottom wall 175. The side walls 174, 176 each include a flange 178, 180, respectively, formed therein for engagement around the top surface 182 of clip cover 122. The reduced height portion 184 of the channel assembly 126 has a slot 164 which extends through a passageway 184 in the knob 138 and matingly engages corresponding annular flange 186 formed in the link 144.

With reference to FIG. 17, elongated pusher bar 134 has a plurality of openings 135 in its distal end to provide flexibility as it advances up the approximately 30 degree incline of the jaws 118. Otherwise the bar 134 is similar as is shown in FIG. 10 for engaging and pushing the last and most proximal clip 158 on the clip carrier 128. The proximal end of the pusher bar 134 includes a slot 208 for receiving a clip indicator 136 which engages a rod 142. A coil spring 148 fits within the molded contours of bottom housing 102 and cooperates with the spring guide 146 to bias and advance pusher bar 134 distally, thereby advancing clips 158. The spring 107 biases the handle 101, 103 in their open position by biasing the handles 101, 103 apart and also biases the channel assembly 126 proximally.

As shown in FIG. 17, a link 144 having an aperture 214 extending longitudinally therethrough translates actuation of the forming cam 154 into movement of the channel 126. An annular flange 186 in the link 144 engages a slot 164 in the channel assembly 126 to actuate the channel 126 in response to movement of the handles. It should be noted that while the flange 186 and slot 164 engagement permits movement of the channel assembly 126 along its longitudinal axis, the slot 164 is also free to rotate about the annular flange 186 in response to rotation of the knob 138. A rod 142 extends, and moves longitudinally through the link 144, but not actuated by the link. The proximal end of the rod 142 engages the spring guide 146 to translate the bias or tension of the spring 148 to the pusher bar 134 by its attachment at its distal end to the clip indicator 136 and hence pusher bar 134.

Referring to FIGS. 17 and 22, the knob 138 retains the proximal ends of and rotates the jaw blade assembly 114, the clips 158, the clip indicator 136, the pusher bar 134 and the clip cover 122. The knob 138 also receives a wedge 150 which provides a friction fit of the jaw blade assembly 114, 134 and clip cover 122 in the knob 138, thereby enabling their rotation in response to rotation of the knob 138.

Turning now to the actuating mechanism of the device 200, each handle 101, 103 is articulated to the housings 102 and 104 and the channel assembly 126 in a similar fashion. More specifically, handles 101, 103 are pivotally connected to opposite sides of the housings 102, 104 and engage pins 108 which ride along cam slots 156 of forming cam 154. The forming cam 154 is connected by a pair of arms 155 at its distal end to the cutouts 196 of the link 144. Since each handle is connected in a similar fashion, only the connection of one of the handles will be discussed. As indicated in FIG. 17, the channel assembly 126 is mounted to the distal end of link 144 while the proximal end of link 144 is attached to the distal end of forming cam 154. Thus, when handles 101, 103 close together, the pins 108 move along slots 156 of forming cam 154 to distally advance the forming cam 154 which correspondingly advances the channel assembly 126 and overcomes the bias of spring 107.

In use, the clip applier 200 is provided with a clip 158 already in the jaws 118 of the jaw blade assembly 114. The clip indicator 136 may be viewed through the window 123 on the clip cover 122 to display approximately how many clips 158 are left in the device 200. To apply the clip 158, the handles 101, 103 are first squeezed together overcoming the bias of spring 107 and causing the channel assembly 126 to move distally and over jaws 118 of the jaw blade assembly 114. As best shown in FIG. 25, this movement over the jaws 118 cams the jaws 118 closed causing the raised portions 120 of the jaws 118 to form the clip 158 therein. The flexibility of the jaws 118 prevents trauma to tissue in which the clip 158 is being applied by not further forming the clip 158 or damaging tissue once the clip 158 has been formed. This trauma is prevented by the jaw arms 149 which absorb the overstroke and deflect once the clip 158 has been fully formed and the jaws 118 are closed, but the channel assembly is still advancing. As the handles 101, 103 open, the formed clip 159 is released from the jaws 118, the pusher bar 134 is advanced distally to advance the next clip 161 to the jaws 118, the clip being retained in the jaws by the raised portions 120.

The distal end of the clip applier 200 may be rotated by rotating the knurled surface 140 of the rotation knob 138 which rotates the channel assembly 126, jaw blade assembly 114, clip cover 122, pusher bar 134 and the indicator 134 mounted therein.

While the preceding paragraphs describe an applier for surgical clips for vascular anastomosis, it should be understood that the applier is not limited to such uses. In fact, applier can also be used for effecting skin closures.

Other variations and modifications of the invention may occur to those of skill in the art. It is therefore intended that the foregoing be regarded as merely illustrative of the invention, which should be measured by the claims that follow.

What is claimed:

1. A surgical clip applicator comprising:
a housing;
a pair of handles pivotally connected to said housing and actuable in a tweezer-like manner, each of said handles having a proximal and a distal end and being pivotally mounted to said housing at said proximal ends;
a pair of jaws extending from said housing for receiving and deforming a clip therebetween;
means extending from said housing for holding a series of clips;
a U-shaped channel assembly slidably mounted in said housing;
means connected to said channel assembly for sliding said channel assembly in a distal direction in response to closing of said handles to move said jaws towards each other;
a pusher bar slidably mounted for movement in a distal direction in said channel assembly for advancing said series of clips along said holding means;
first spring means connected between said handles for biasing said channel assembly in a proximal direction;
second spring means biasing said pusher bar in a distal direction to urge said series of clips in a distal direction to push a foremost clip from said series of clips to a position between said jaws; and
means for translating tension of said second spring means to said pusher bin.

2. A surgical clip applicator as defined in claim 1 wherein said jaws and said clip holding means are integral.

3. A surgical clip applicator as defined in claim 1 wherein said first spring means biases said handles into an opened position.

4. A surgical clip applier as defined in claim 1 wherein said distal end of said pusher bar has a rounded distal end portion with a pair of prongs for engaging the proximal-most clip on said clip holding means.

5. A surgical clip applier as defined in claim 1 further comprising rotation control means for effectuating independent rotation of said clip holding means; said channel assembly and said pusher bar.

6. A surgical clip applier as defined in claim 5 wherein said rotation control means further comprises a wedge for retaining said clip holding means, said channel assembly and said pusher bar within said rotation control means.

7. A surgical clip applier as defined in claim 6 wherein said translating tension means is a rod which rotates in response to said rotation control means.

8. A surgical clip applier as defined in claim 1 wherein said handles are pivotable about a distal end of said housing.

9. A surgical clip applicator as defined in claim 1, further comprising a spring guide cooperating with said second spring means for controlling advancement of said pusher bar.

10. A surgical clip applier comprising:
a housing;
a pair of handles pivotally connected to said housing and actuable in a tweezer-like manner, each of said handles having a proximal and a distal end and being pivotally mounted to said housing at said proximal ends;
a pair of jaws extending from said housing for receiving and deforming a clip therebetween;
means extending from said housing for housing a series of clips;
a U-shaped channel assembly slidably mounted in said housing;
means connected to said channel assembly for sliding said channel assembly in a distal direction in response to closing of said handles to move said jaws towards each other;
a pusher bar slidably mounted in said channel assembly for advancing said series of clips along said holding means;
first spring means connected between said handles for biasing said channel assembly in a proximal direction;
second spring means biasing said pusher bar in a distal direction to push a foremost clip from said clip holding means to a position between said jaws; and
means for translating tension of said second spring means to said pusher bar wherein said sliding means includes at least one cam slot for engaging with said handles to actuate said channel assembly.

11. A surgical clip applicator comprising:
a housing;
a pair of handles pivotally connected to said housing, each of said handles having a proximal and a distal end and being pivotally mounted to said housing at said proximal ends;
a pair of jaws extending from said housing for receiving and deforming a clip therebetween;
means extending from said housing for holding a series of clips;
a U-shaped channel assembly slidably mounted in said housing;
means connected to said channel assembly for sliding said channel assembly in a distal direction in response to closing of said handles to move said jaws towards each other;

a pusher bar slidably mounted for movement in a distal direction in said channel assembly for advancing said series of clips along said holding means;

first spring means connected between said handles for biasing said channel assembly in a proximal direction;

second spring means biasing said pusher bar in a distal direction to urge said series of clips in a distal direction to push a foremost clip from said series of clips to a position between said jaws; and means operatively associated with said housing for rotating said jaws with respect to said housing.

12. A surgical clip applier as defined in claim 11 wherein said jaws and said clip holding means are integral.

13. A surgical clip applier as defined in claim 11 wherein said first spring means biases said handles into an opened position.

14. A surgical clip applier as defined in claim 11 further comprising a wedge means for engaging said jaws, clip holding means and channel assembly within said rotating means.

15. A surgical clip applier as defined in claim 11 wherein said sliding means includes at least one cam slot for engaging with said handles to actuate said channel assembly.

16. A surgical clip applier as defined in claim 11 wherein said handles are pivotable about a distal end of said housing.

17. A surgical clip applicator comprising:

a housing;

a pair of handles pivotally connected to the housing, each of the handles having a proximal and a distal end and being pivotally mounted to the housing at the proximal end;

a jaw blade assembly including a pair of jaws and a clip carrier, the jaw blade assembly extending from the housing and receiving and deforming a clip therebetween;

a U-shaped channel assembly slidably mounted in the housing;

a camming member connected to the channel assembly, the camming member sliding the channel assembly in a distal direction in response to closing of the handles to move the pair of jaws towards each other;

a pusher bar movable toward the jaws to urge the series of clips towards the jaws moving to advance the series of clips along the clip carrier;

a first spring connected between the handles, the first spring biasing the camming member and the channel assembly in a proximal direction; and a second spring associated with the pusher bar, the second spring biasing the pusher bar in a distal direction to urge the series of clips in a distal direction along the clip carrier to push a foremost clip from the series of clips to a position between the jaws;

wherein the handles are operatively connected to the camming member, such that closing the handles drives the camming member and the channel assembly in a distal direction to close the jaws and crimp a clip positioned therebetween.

18. A surgical clip applicator comprising:

a housing and an elongated body portion extending therefrom;

a pair of handles pivotally connected to the housing;

a pair of jaws having a clip receiving portion positioned distally of the elongated body portion, the jaws being relatively movable from an open position to a closed position;

a series of clips arranged in end-to-end relation, wherein in the open position, the jaws are configured to receive a clip from the series of clips and in the closed positions, the jaws deform the clip positioned therebetween;

a pusher bar movable toward the jaws to urge the series of clips towards the jaws; and a biasing member cooperating with the pusher bar, the biasing member being positioned to continuously urge the pusher bar and the series of clips towards the jaws to position a distal-most clip from the series of clips between the jaws when the jaws are open and to maintain the distal-most clip in position between the jaws at least until the distal-most clip has been partially deformed.

19. A surgical clip applicator as defined in claim 18 further including a jaw blade extending from the distal end of the housing, the pair of jaws being positioned at the distal end of the jaw blade.

20. A surgical clip applicator as defined in claim 19, wherein the series of clips is supported on the jaw blade.

21. A surgical clip applicator as defined in claim 18 wherein each clip in the series of clips is positioned to continuously engage adjacent clips.

22. A surgical clip applicator as defined in claim 18 wherein each of the handles has a proximal end and a distal end, the proximal end of the handles being pivotably mounted to the housing such that the handles are actuable in a tweezer-like manner.

23. A surgical clip applicator as defined in claim 18, further comprising a channel assembly slidably mounted with respect to the housing and the pair of jaws and adapted for slidable movement into engagement with the jaws to move the jaws from the open position to the closed position to deform a clip positioned therebetween.

24. A surgical clip applicator as defined in claim 23 further comprising a forming cam operatively connected between the channel assembly and the pair of handles such that when the handles are pivoted toward the housing, the forming cam is moved distally to move the channel assembly distally.

25. A surgical clip applicator as defined in claim 24 wherein the forming cam includes at least one cam slot which interacts with a pin connected to the pair of handles to move the channel assembly distally.

26. A surgical clip applicator as defined in claim 24 further comprising a spring positioned to bias the handles outwardly to move the channel assembly and the forming cam in a proximal direction.

27. A surgical clip applicator as defined in claim 23 further comprising a window formed in the housing and a rotatable member having a throughbore; positioned in the window, the channel assembly, pair of jaws, and pusher bar being secured within the throughbore to facilitate rotation thereof.

28. A surgical clip applicator as defined in claim 18 wherein the biasing member is positioned within the housing, and wherein the applicator further comprises a rod extending between the biasing member and the pusher bar to urge the pusher bar distally.

29. A surgical clip applicator as defined in claim 18 wherein the pusher bar is positioned proximal of the proximal-most clip from the series of clips and remains in this position as it urges the distal-most clip between the jaws.

30. A surgical clip applicator comprising:

a housing and an elongated body portion extending therefrom;

a pair of handles pivotally connected to the housing, each of the handles having a proximal end and a distal end and being pivotally mounted to the housing at their proximal ends, the handles being actuable in a tweezer-like manner;

a pair of jaws having a clip receiving portion positioned distally of the elongated body portion, the clip receiving portion being configured to receive a clip from a series of clips, the jaws being movable between an open position and a closed position to deform a clip positioned therebetween;

a pusher bar engaging a clip to urge the series of clips towards the pair of jaws; and an actuating mechanism operably connected to the handles, the actuating mechanism being movable to move the jaws between the open and closed positions.

31. A surgical clip applicator as defined in claim 30 further comprising a biasing member positioned to urge the pusher bar and the series of clips towards the jaws to position the distal-most clip of the series of clips between the pair of jaws when the jaws are in the open position.

32. A surgical clip applicator as defined in claim 30 further comprising a channel assembly slidably positioned within the housing and being movable into engagement with the jaws to move the jaws from the open position to the closed position.

33. A surgical clip applicator as defined in claim 32 wherein the actuating mechanism includes a forming cam operatively connected between the channel assembly and the pair of handles, the forming cam being configured to move the channel assembly distally in response to inward pivoting of the handles.

34. A surgical clip applicator as defined in claim 33 wherein the forming cam includes at least one cam slot and is slidably positioned in the housing, the pair of handles having at least one pin positioned within the cam slot.

35. A surgical clip applicator as defined in claim 33 wherein the forming cam includes a pair of cam slots and each of the handles includes a pin positioned within a respective one of the cam slots.

36. A surgical clip applicator as defined in claim 32 further comprising a rotatable member rotatably connected to the housing and having a throughbore configured to support the channel assembly, the pair of jaws, and the pusher bar to facilitate rotation thereof.

37. A surgical clip applicator as defined in claim 36, wherein the actuating mechanism includes a non-rotatable link operatively connected to the channel assembly to permit rotation of the channel assembly, the link being slidable longitudinally to permit longitudinal movement of the channel assembly.

38. A surgical clip applicator comprising:

a housing and an elongated body portion extending therefrom;

a pair of handles pivotally connected to the housing;

a pair of jaws having a clip receiving portion positioned distally of the elongated body portion, the jaws being relatively movable from an open position to a closed position;

a series of clips arranged in end-to-end relation, wherein the open position, the jaws are configured to receive a clip from the series of clips and in the closed position, the jaws deform the clip positioned therebetween;

a pusher bar mounted for movement only in the distal direction to urge the series of clips towards the jaws; and a biasing member cooperating with the pusher bar, the biasing member being positioned to urge the pusher bar and the series of clips towards the jaws to position a distal-most clip from the series of clips between the jaws when the jaws are in the open position.

39. A surgical clip applicator as defined in claim 38 further comprising a channel assembly positioned within the housing and being movable into engagement with the jaws to move the jaws from the open position to the closed position.

40. A surgical clip applicator as defined in claim 39 further comprising a rotatable member having a throughbore supported on the housing, the channel assembly, the pair of jaws, and the pusher bar being secured within the throughbore to facilitate rotation thereof.

41. A surgical clip applicator comprising:

a housing;

a pair of handles pivotally connected to the housing;

a pair of jaws extending from a distal end of the housing, the jaws being relatively movable from an open position to a closed position;

a series of clips arranged in end-to-end relation, wherein in the open position, the jaws are configured to receive a clip from the series of clips and in the closed positions, the jaws deform the clip positioned therebetween;

a pusher bar movable toward the jaws to urge the series of clips towards the jaws;

a biasing member cooperating with the pusher bar, the biasing member bearing positioned to urge the pusher bar and the series of clips towards the jaws to position a distal-most clip from the series of clips between the jaws when the jaws are open and to maintain the distal-most clip in position between the jaws at least until the distal-most clip has been partially deformed; and a channel assembly slidably mounted with respect to the housing and the pair of jaws and adapted for slidable movement into engagement with the jaws to move the jaws from the open position to the closed position to deform a clip positioned therebetween.

42. A surgical clip applicator as defined in claim 41, wherein each of the handles has a proximal and a distal end, the proximal end of the handles being pivotally mounted to the housing such that the handles are actuable in a tweezer-like manner.

43. A surgical clip applicator as defined in claim 41 further comprising a rotatable member supported on the housing, the pair of jaws being operably connected to the rotatable member to facilitate rotation of the pair of jaws.

44. A surgical clip applicator as defined in claim 41 wherein the pusher bar is positioned proximal of the proximal-most clip from the series of clips and remains in this position as it urges the distal-most clip from the series of clips between the jaws.

45. A surgical clip applicator comprising:

a housing;

a pair of handles pivotally connected to the housing;

a pair of jaws extending from a distal end of the housing, the jaws being relatively movable from an open position to a closed position;

a series of clips arranged in end-to-end relation, wherein in the open position, the jaws are configured to receive a clip from the series of clips and in the closed position, the jaws deform the clip positioned therebetween;

a pusher bar mounted for movement only in the distal direction to urge the series of clips towards the jaws;

a biasing member cooperating with the pusher bar, the biasing member being positioned to urge the pusher bar and the series of clips towards the jaws to position a distal-most clip from the series of clips between the jaws when the jaws are in the open position; and a channel assembly positioned within the housing and being movable into engagement with the jaws to move the jaws from the open position to the closed position.

46. A surgical clip applicator as defined in claim 45 wherein each of the handles has a proximal end and a distal end, the proximal end of the handles being pivotably mounted to the housing such that the handles are actuable in a tweezer-like manner.

47. A surgical clip applicator as defined in claim 45 further comprising a rotatable member supported on the housing, the pair of jaws being operably connected to the rotatable member to facilitate rotation thereof.

48. A surgical clip applicator according to claim 45 wherein the pusher bar is positioned proximal of the proximal-most clip from the series of clips and remains in this position as it urges the distal-most clip from the series of clips between the jaws.

* * * * *